(12) United States Patent
Tsao et al.

(10) Patent No.: US 7,811,571 B2
(45) Date of Patent: Oct. 12, 2010

(54) POLYALLYLAMINE CONJUGATES AND APPLICATIONS THEREOF FOR BIOLOGICAL SIGNAL AMPLIFICATION

(75) Inventors: Chao Yun Tsao, Taipei (TW); Li Te Yin, Taipei (TW); Su Fung Chiou, Keelung (TW); Chung We Pan, Pingtung County (TW); Jia Huey Tsao, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 347 days.

(21) Appl. No.: 10/964,713

(22) Filed: Oct. 15, 2004

(65) Prior Publication Data

US 2005/0106649 A1 May 19, 2005

(30) Foreign Application Priority Data

Nov. 13, 2003 (TW) ............................... 92131838 A

(51) Int. Cl.
*A61K 39/00* (2006.01)
(52) U.S. Cl. ................................. 424/178.1; 424/179.1
(58) Field of Classification Search ........................ None
See application file for complete search history.

(56) References Cited

U.S. PATENT DOCUMENTS 5,711,915 A * 1/1998 Siegmund et al. .......... 422/68.1

OTHER PUBLICATIONS

Boussif et al., Synthesis of polyallylamine derivatives and their use as gene transfer vectors in vitro., Bioconjug Chem., Sep.-Oct. 1999;10(5):877-83.*

Suh et al., Functional molecules based on polyazometals (1) artificial metalloproteinases prepared by conjugation of polyazometals with poly(allylamine), Bioorganic & Medicinal Chemistry Letters, 1998, 8: 2751-2756.*

Ngo et al., in The Protein Folding Problem and Tertiary Structure Prediction, 1994, Merz et al. (ed.), Birkhauser, Boston, MA, pp. 433 and 492-495.*

Boussif et al., Synthesis of polyallylamine derivatives and their use as gene transfer vectors in vitro, Bioconjugate Chem. 10, 877-883, 1999.*

DeSantis et al. (Chemical modifications of enzymes of enhanced functionality, Current Opinion in Biotechnology, vol. 10, Issue 4, Aug. 1999, pp. 324-330).*

Sommer et al. (Clin. Chem. 36, 201-206, 1990).*

Taira et al. Self-assembled DNA-conjugated polymer for novel DNA chip, Analytical Sciences, Jan. 2003, vol. 19, pp. 177-179.*

Satoh et al. (Simultaneous determination of alpha-lipoic acid and its reduced form by high-performance liquid chromatography with fluorescence detection, Journal of Chromatography B, 854 (2007) 109-115).*

* cited by examiner

*Primary Examiner*—Suzanne M Noakes
*Assistant Examiner*—Jae W Lee
(74) *Attorney, Agent, or Firm*—Bacon & Thomas, PLLC

(57) ABSTRACT

Polyallylamine conjugates and applications thereof for biological signal amplification are provided by utilizing the essential amino group of polyallylamine to covalently bind with capture agents and signal molecules having the functional groups selected from a group consisting of —NHS, —CO, —S=$O_2$ and —C=O—C=O. The resulting conjugates having more than one signaling entities can be further implemented for biological expression with enhancing effect on biological signal intensity, such that the sensitivity of detection for the variation between biological interactions is largely increased.

15 Claims, 5 Drawing Sheets

POLYALLYLAMINE CONJUGATES AND APPLICATIONS THEREOF FOR BIOLOGICAL SIGNAL AMPLIFICATION

BACKGROUND OF THE INVENTION

1. Field of the Invention

The present invention relates to polyallylamine conjugates and applications thereof for biological signal amplification, which enhance the biological signal intensity of trace molecules by utilizing the amino group of polyallylamine repeating unit to covalently bind with signal molecules and capture agents.

2. Description of Related Art

Spurred by the vigorous development of biomedical technology, broadened research fields and rapid expansion of applications, a great number of screening procedures have been developed. The most notable of them is the mapping of human genomes, followed by the successful applications of gene chips in the study of gene functionality. However, cell physiology is in fact affected by proteins. Unlike working on mRNA level, proteins in cells would interact with other proteins, small molecules or drugs, or perform other functions only after undergoing post-translation modification and sorting. That information on the mechanism of protein interactions is not obtainable independently; making the development of protein chips all the more important. Currently protein chips are applied in immunoanalysis, research of protein-to-protein interaction, research of gene expression mechanism, and cell-to-cell interaction. In light that the functional activity of protein is related to its stereo structure, making protein chip is a more complex than making gene chip. Aside from modeling after the DNA chip technology, there are quite a few key technologies to overcome in the making of protein chips, for examples: (1) How to immobilize biologically active protein on the chip? (2) How to identify the immobilized trace protein? (3) How to obtain definitive detection results from trace protein? As for the third technical problem, protein is different from DNA or RNA, which may be amplified by means of polymerase chain reaction (PCR). Thus it is rather important to grasp the technique for detecting low level of protein that binds on the chip.

U.S. Pat. No. 5,891,741 discloses the use of a dextran or polylysine conjugate to amplify the biological signals. But when dextran or polylysine is employed, self-quenching of fluorescence emission from the signal molecules, that is, the fluorescent molecules bound on the same polymer molecule, occurs due to short distances between the fluorescent molecules. The resulting offset of the original signal intensity weakens the signal expression instead. In addition, the short chain length of polylysine tends to create steric hindrance, while dextran requires modification, such as peroxidation to generate —COH or increasing —NH or other functional groups to aid its binding with the signal molecules, in which the degree of peroxidation poses another big variable. Thus the signal amplification procedure using dextran or polylysine is both complicated and hard to control.

SUMMARY OF THE INVENTION

To address the drawback of prior art of biological signal amplification, this invention utilizes polyallylamine as base of conjugate for signal amplification, in which the distance between the functional groups of polyallylamine is controlled by controlling the length of carbon chain in the synthesis process. A preferred embodiment of this invention has the backbone of (—NH$_2$—CH$_2$—CH$_2$═CH—)n and repetitive branched chains of —NH$_2$ with the following structural formula (I):

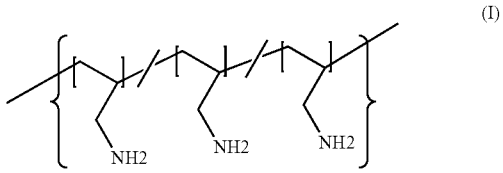

This invention utilizes the covalent binding of the aforesaid —NH$_2$ with signal molecules and capture agents to form a conjugate capable of intensifying biological signals. The weak signal of target protein can be amplified by said conjugates, such that the purpose of protein identification is achieved.

The objective of this invention is to provide a polyallylamine conjugate which comprises polyallylamine, signal molecules and capture agents; wherein each signal molecule and capture agent is attached to the polyallylamine via a —NH$_2$ side chain of the polyallylamine.

As used herein, the signal molecules used in the present invention comprise enzyme, fluorescent molecules, luminescent molecules or other biologically signaling substances. The capture agents used in the present invention comprise protein, antigen, antibody, nucleic acid or other biomolecules with binding specificity.

Another objective of this invention is to provide a method for preparing polyallylamine conjugates, comprising the steps of: (a) binding polyallylamine with signal molecules having functional groups selected from a group consisting of —NHS, —CO, —S═O$_2$ and —C═O—C═O; (b) purifying the resulting product from step (a); (c) binding the purified product from step (b) with capture agents; and (d) purifying the resulting product from step (c) to obtain a polyallylamine conjugate having polyallylamine, signal molecules and capture agents.

According to the method for preparing polyallylamine conjugates of the invention, wherein the signal molecules of the step (a) are bound with the —NH$_2$ of polyallylamine; the capture agent of the step (c) are bound with the —NH$_2$ of polyallylamine directly or indirectly.

In one embodiment, before used in the step (c), the capture agent can be modified, if desired, by compounds having functional groups selected from a group consisting of —SH, —CO, —NH$_2$ and —N═C═S and mixed with proper cross-linking agent or catalyst to assist the binding of capture agent with the —NH$_2$ of polyallylamine. Said cross-linking agent mixed with modified capture agent is a compound selected from a group consisting of N-succinimidyl 3-(2-pyridyldithio) propionate, glutaraldehyde, succinimidyl-4-)N-maleimidomethyl)cyclohexane-1-carboxylate (SMCC), maleimide, iodoacetamide, protected thiol, sulfosuccinimidyl-6-(3'-[2-pyridyldithio]propionamido)hexanoate (sulfo-LC-SPDP).

The purification method used in step (b) or (d) of said method according to the invention comprises, but not limited to, chromatography, centrifugation and precipitation or other methods used to achieve the purpose of separation.

Yet another objective of this invention is to provide a method for amplifying biological signals, comprising the steps of: (a) binding polyallylamine with signal molecules having functional groups selected from a group consisting of —NHS, —CO, —S═O$_2$ and —C═O—C═O; (b) purifying the resulting product from step (a); (c) binding the purified product from step (b) with capture agents; (d) purifying the resulting product from step (c) to obtain a polyallylamine conjugate containing polyallylamine, signal molecules and capture agents; and (e) binding the resulting polyallylamine conjugate from step (d) with target molecules. Accordingly, the biological signals are amplified. In the step (e) of said method for amplifying biological signals of the present invention, wherein the capture agents of the polyallylamine conjugate can identify the target molecules and combine with them, through those mechanism, the biological signals are amplified. Said target molecules identified by capture molecules are biological molecules, which can be immobilized on a biochip or contained in an assay specimen, such as protein, antigen, antibody, nucleic acid or other biomolecules with binding specificity.

This invention utilizes polyallylamine as base of the conjugate compound for amplification of biological signals, wherein the distance between the functional groups of polyallylamine is controlled by controlling the length of carbon chain in the synthesis process. This approach is free of the problem associated with the use of dextran or polylysine where the distance between the functional groups of the polymer molecule cannot be controlled and hence free of the phenomenon of self-quenching of fluorescence emission from the signal molecules caused by short distances between the adjacent signal molecules. Moreover, compared with dextran, the process of polyallylamine preparation lacks of the modification step, due to the —$NH_2$ group of polyallylamine, and shortens the time for preparation consequently. Therefore, the purpose of time saving and signal amplifying is achieved simultaneously.

DETAILED DESCRIPTION OF THE INVENTION

Figure 1:
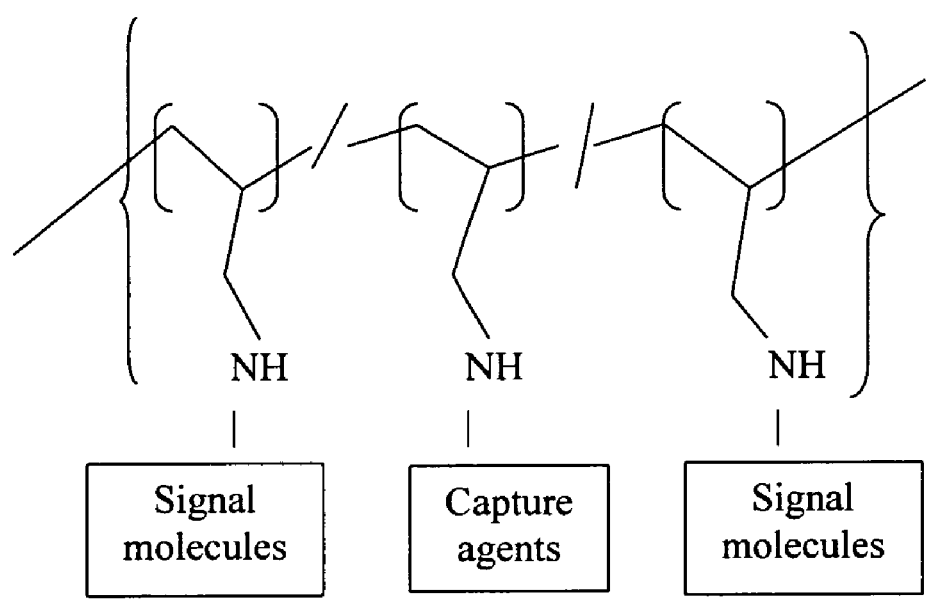
FIG. 1 shows the structural diagram of polyallylamine conjugate according to the present invention.

The polyallylamine conjugate of the present invention that may be applied in amplification of biological signals comprises polyallylamine having the backbone of (—$NH_2$—$CH_2$—$CH_2$=CH—)n and repetitive branched chains of —$NH_2$; signal molecules for detection; and capture agents for identifying the target molecules; wherein each signal molecule and capture agent is attached to the polyallylamine via a —$NH_2$ side chain of the polyallylamine. FIG. 1 shows the structural diagram of this polyallylamine conjugate, wherein the signal molecules can be enzyme, fluorescent molecules, luminescent molecules or other biologically signaling substances, and the capture agent can be protein, antigen, antibody, nucleic acid or other biomolecules with binding specificity.

Figure 2:
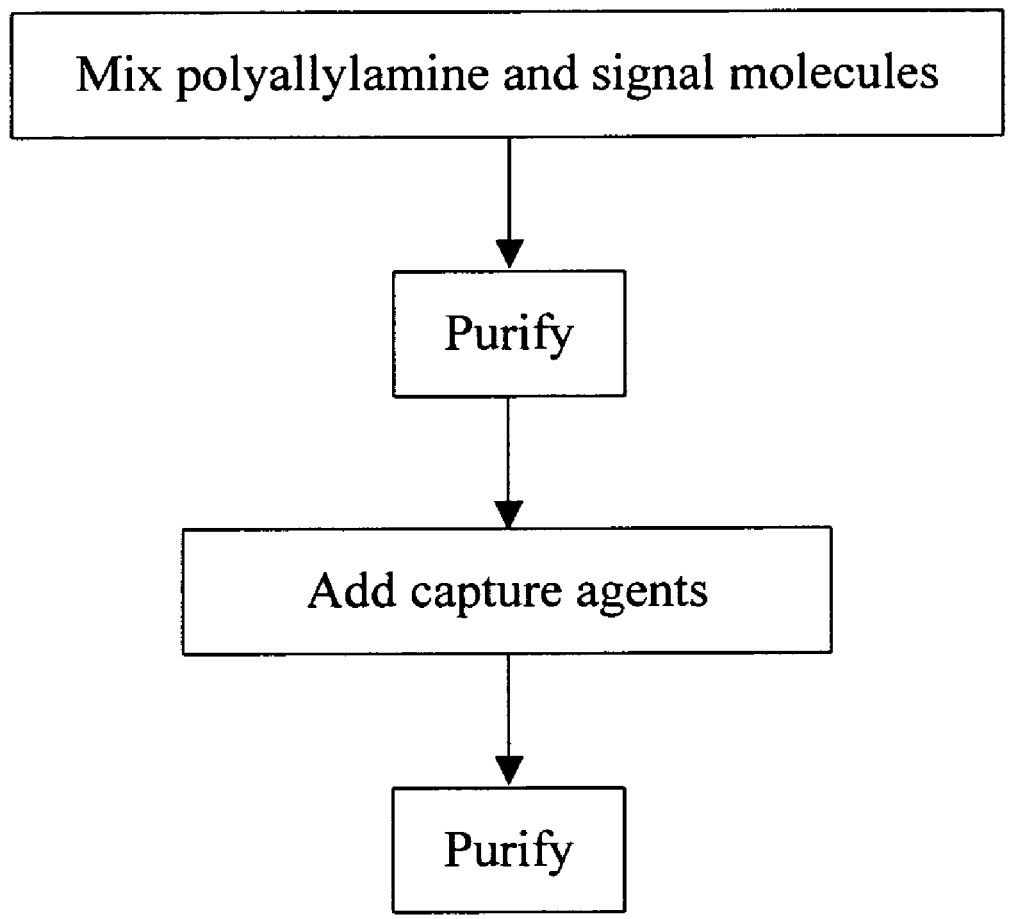
FIG. 2 shows the flow chart for the preparation of polyallylamine conjugate according to the present invention.

FIG. 2 shows the process for preparing the polyallylamine conjugate. First, mix polyallylamine with signal molecules having functional groups selected from a group consisting of —NHS, —CO, —S=$O_2$ and —C=O—C=O, in which the —$NH_2$ of polyallylamine react and bind with the functional groups of signal molecules, and the signal molecules may be enzyme, fluorescent molecules, luminescent molecules, or other biologically signaling substance; next purify the reaction product of polyallylamine and signal molecules by means of column chromatography, precipitation or other separation methods; then add capture agents (e.g. protein, antigen, antibody, or nucleic acid et al.) into the purified polyallylamine-signal molecules conjugates, wherein the capture agents bind with polyallylamine directly or indirectly through —$NH_2$; and finally purify the product added with capture agents to obtain a polyallylamine conjugate containing polyallylamine, signal molecules and capture agents.

The aforesaid capture agent can be bound with the —$NH_2$ of polyallylamine optionally by chemical modification (for example, modified by —SH, —CO, —$NH_2$, or —N=C=S) and cross-linking agent (e.g. SPDP or glutaraldehyde) or catalyst mixing.

Figure 3:
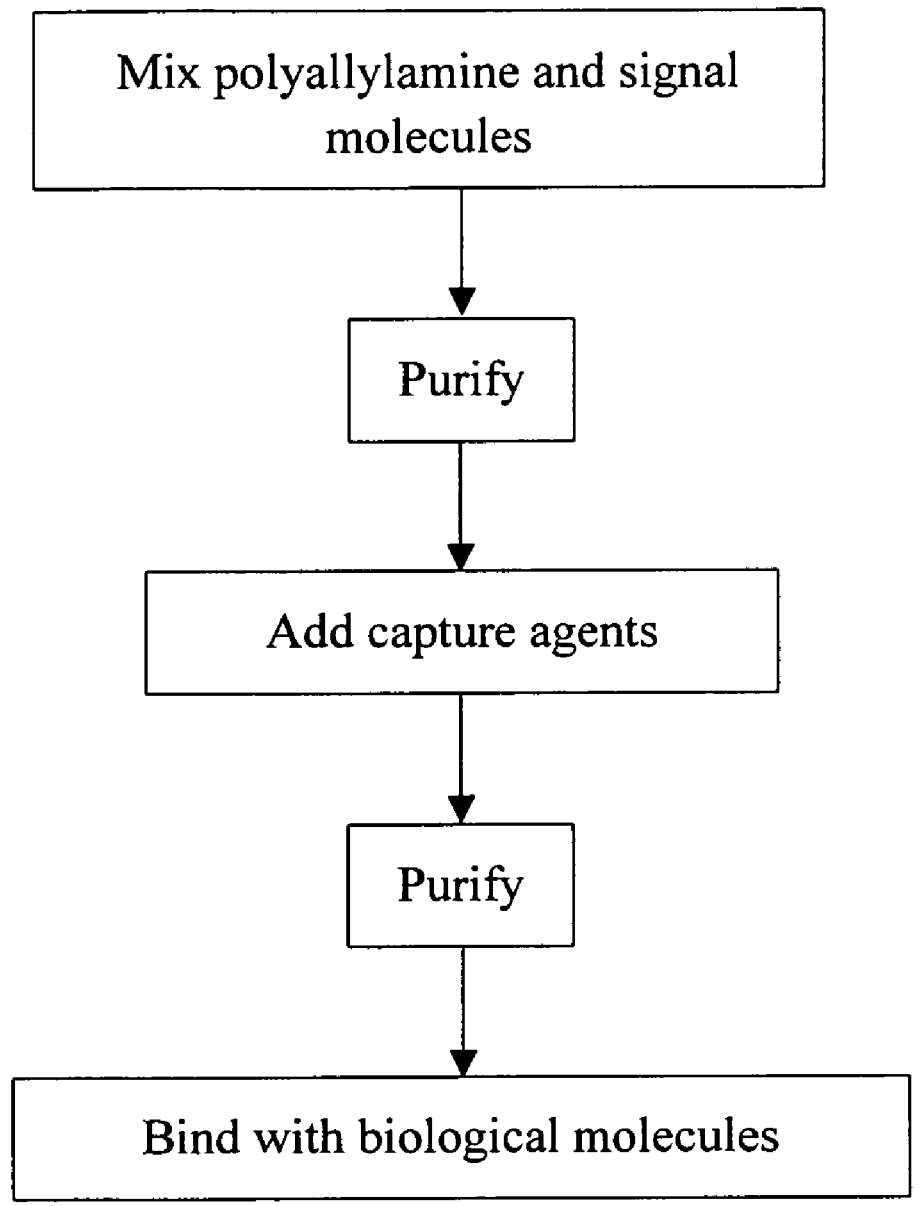
FIG. 3 shows the flow chart for the method of biological signal amplification.

FIG. 3 shows the method for amplifying biological signals. First mix polyallylamine with signal molecules (e.g. enzyme, fluorescent molecules, or luminescent molecules), in which the —$NH_2$ groups of polyallylamine react and bind with the functional groups of signal molecules; next purify the reaction product of polyallylamine and signal molecules; then add capture agents (e.g. protein, antigen, antibody, or nucleic acid) into the purified conjugate of polyallylamine and signal molecules, wherein the capture agents bind with polyallylamine directly or indirectly through —$NH_2$; then purify the product added with capture agents to obtain a polyallylamine conjugate containing polyallylamine, signal molecules and capture agents; and finally put the polyallylamine conjugate in contact with target molecules (e.g. antigen on a biochip), where the capture agents (e.g. antibody) in the conjugate can identify the target molecules and bind the target to the conjugate through specific reaction between the capture agents and the target molecules (e.g. antigen-antibody interaction) and the signals of the target molecules are amplified by signal molecules in the conjugate, such that the sensitivity of detecting low levels of biological molecules is enhanced.

The polyallylamine conjugate of the present invention and its applications for biological signal amplification are further illustrated in examples below.

EXAMPLE 1

This example provides a method for preparing polyallylamine conjugate as described below, in which fluorescence reagent cy5 was chosen as signal molecules, modified anti-IgE-(SH)n was the capture agent, and added cross-linking agent SPDP to assist the binding of capture agent with the polyallylamine so as to obtain a polyallylamine conjugate.

(A) Preparation of $(SPDP)_n$-PAA-$(cy5)_n$

Prepare 10 mg/ml polyallylamine (PAA, MW=65 k, Aldrich Chemical) solution with 0.1M phosphate buffered saline (PBS; pH 7.4; see Sambrook, et al., Molecular Cloning, A Laboratory Manual, Cold Spring Harbor Laboratory Press, New York, 2001 for its preparation) and add ½ tube cy5-NHS (Amersham Biosciences). After reaction for 90 minutes under ambient temperature, separate unreacted cy5-NHS with PD-10 column and measure the absorption spectrum of collected fractions using spectrophotometer (200~650 nm). Choose fractions that show absorbance at 208 nm and 650 nm simultaneously. Add SPDP (Pierce Co.) to the fractions. After reaction for 60 minutes, use PD-10 column to remove unreacted SPDP.

(B) Preparation of Antibody-(SH)n

Add 200 μg of anti-IgE (Lenico Co.) to 5.5 μl (1 mg/1 ml) of 2-iminothiolane-HCL (Lenico Co.). After reaction for 45 minutes under ambient temperature, separate unreacted 2-iminothiolane-HCl using a PD-10 column. Subject the collected fractions to spectrophotometer and quantify the antibody from absorbance at 280 nm.

(C) Preparation of Polyallylamine Conjugate

Mix the resulting products from (A) and (B) above and let them react for 60 minutes under ambient temperature. Remove unreacted antibody-(SH)n using column chromatography to obtain polyallylamine conjugate containing polyallylamine, signal molecules and capture agents.

EXAMPLE 2

Prepare 10 mg/ml polyallylamine (PAA) solution with 0.1M PBS buffer (pH 7.4). Add ½ tube cy5-NHS to 50 µl PAA solution. After reaction for 90 minutes under ambient temperature, remove unreacted cy5-NHS with PD-10 column and measure the absorption spectrum of collected fractions using spectrophotometer (200~650 nm). Choose fractions that show absorbance at 208 nm and 650 nm simultaneously to obtain purified PAA-cy5 compound. Serially dilute the synthesized PAA-cy5 (0.2 mg/ml) described above and dextran-cy5 having the same concentration by a factor of 10 each time (1, ¹⁄₁₀, ¹⁄₁₀₀, ¹⁄₁₀₀₀, and ¹⁄₁₀₀₀₀), and compare the fluorescence intensity of the solutions using microarray scanner GenePix4000B. The results are shown in FIG. 4A and FIG. 4B.

Figure 4A:
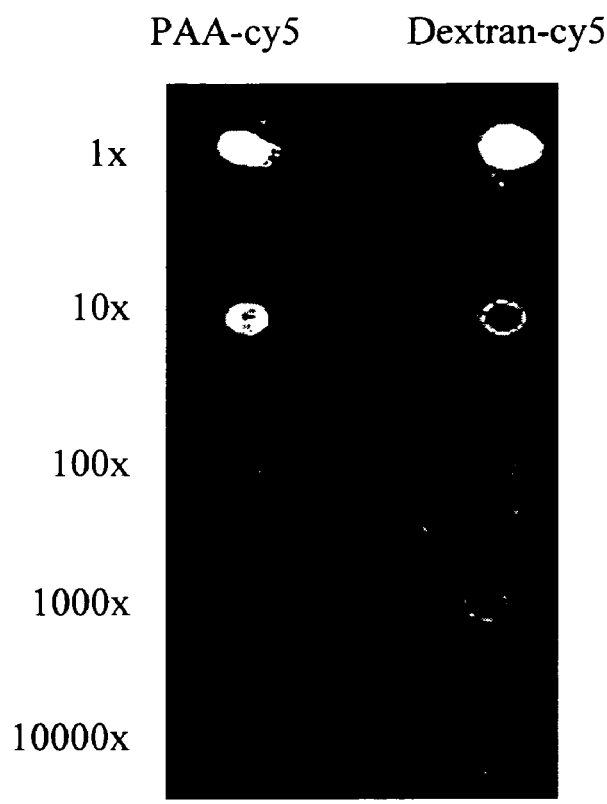
FIG. 4A shows the image of signal molecules after the synthesis of PAA-cy5 and dextran-cy5.
Figure 4B:
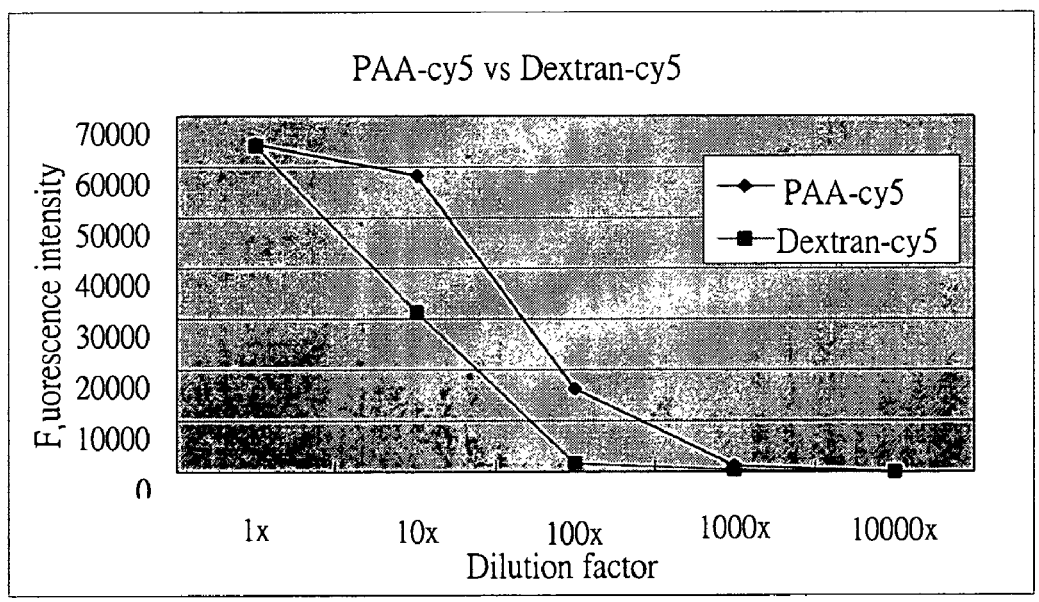
FIG. 4B compares the line graphs of fluorescence intensity versus dilution factor of PAA-cy5 and dextran-cy5.

FIG. 4A shows the respective images of signal molecules of PAA-cy5 and dextran-cy5 at different concentrations. FIG. 4B compares the line graphs of fluorescence intensity versus dilution factor of PAA-cy5 and dextran-cy5 in serial dilution, which shows that signals could be detected at trace amount of PAA-cy5.

EXAMPLE 3

This example describes the application of polyallylamine conjugate synthesized according to Example 1 on biochip to amplify biological signals. First immobilize staphylococcal protein A onto a chip (37° C., 1 hour), wash off protein A not attached to the chip, and add 10-fold dilution of polyallylamine conjugate (anti-IgE-PAA-cy5) synthesized according to Example 1. After reaction for 1 hour under 37° C., wash off unreacted polyallylamine conjugate, and scan the chip with GenePix4000B. The results are shown in FIG. 5A and FIG. 5B.

Figure 5A:
FIG. 5A shows the specificity of staphylococcal protein A to antibody.
Figure 5B:
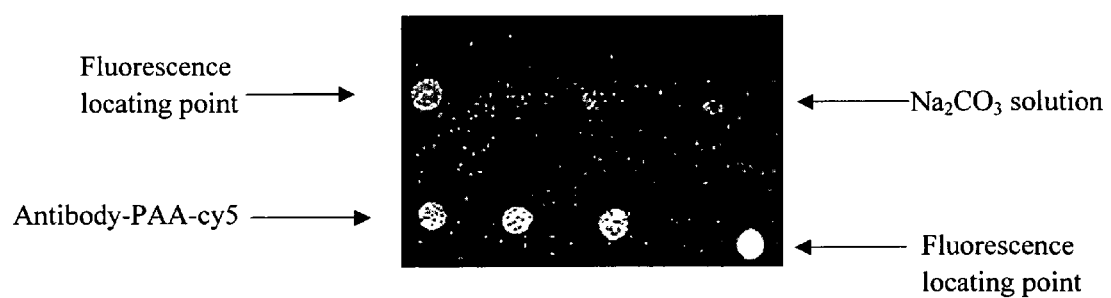
FIG. 5B shows the image of chip after signal amplification by polyallylamine conjugate.

FIG. 5A is an image of the binding specificity of staphylococcal protein A to antibody, showing that staphylococcal protein A bind with antibody specifically. When 0.1M PBS (pH 7.4) was used as control, staphylococcal protein A did not show non-specific binding, which tends to lead to false positive (signal) reaction. FIG. 5B shows the image of chip after polyallylamine conjugate was added for amplification of biological signal. The upper row shows the results of using 0.1M sodium carbonate (pH 9.4) as control, and the bottom row shows the results of using polyallylamine conjugate for signal amplification. As compared to the control, the location of protein on the chip was clearly identified after reaction with polyallylamine conjugate, and the signal molecules in the conjugate allow signal detection by instrument. As analyzed by GenePix4000B software, the signal/noise ratio obtained was 62047.0 for polyallylamine conjugate and 1098 for the control. Thus the signal intensity after amplification by polyallylamine conjugate was 60 times that of the control, which facilitates detection.

What is claimed is:

1. A polyallylamine conjugate, consisting of polyallylamine, a signal molecule, and a capture agent, wherein said signal molecule is a fluorescent molecule which is cy5; said capture agent is a modified antibody linked to a cross-linking agent, wherein the antibody is modified by a compound having functional groups selected from the group consisting of —SH, —CO, —NH$_2$ and —N=C=S, and a cross-linking agent selected from the group consisting of N-succinimidyl 3-(2-pyridyldithio) propionate, glutaraldehyde, succinimidyl-4-(N-maleimidomethyl)cyclohexane-1-carboxylate (SMCC), maleimide, iodoacetamide, protected thiol and sulfosuccinimidyl-6-(3'-[2-pyridyldithio] propionamido) hexanoate (sulfo-LC-SPDP), and wherein said cross-linking agent assists the binding of said capture agent with the —NH$_2$ functional groups of polyallylamine; and the signal molecule and capture agent is covalently bound to the polyallylamine via —NH$_2$ side chain of the polyallylamine.

2. A polyallylamine conjugate, consisting essentially of polyallylamine, a signal molecule, and a capture agent, wherein said signal molecule is a fluorescent molecule which is cy5; said capture agent is a modified antibody linked to a cross-linking agent, wherein the antibody is modified by a compound having functional groups selected from the group consisting of —SH, —CO, —NH$_2$ and —N=C=S, and a cross-linking agent selected from the group consisting of N-succinimidyl 3-(2-pyridyldithio) propionate, glutaraldehyde, succinimidyl-4-(N-maleimidomethyl)cyclohexane-1-carboxylate (SMCC), maleimide, iodoacetamide, protected thiol and sulfosuccinimidyl-6-(3'-[2-pyridyldithio] propionamido) hexanoate (sulfo-LC-SPDP), and wherein said cross-linking agent assists the binding of said capture agent with the —NH$_2$ functional groups of polyallylamine; and the signal molecule and capture agent is covalently bound to the polyallylamine via —NH$_2$ side chain of the polyallylamine.

3. The polyallylamine conjugate according to claim 1, wherein the polyallylamine conjugate is in contact with a target molecule.

4. The polyallylamine conjugate according to claim 3, wherein the target molecule is an antigen or on a biochip.

5. The polyallylamine conjugate according to claim 4, wherein the target molecule is an antigen.

6. The polyallylamine conjugate according to claim 2, wherein the antibody is an anti-IgE antibody.

7. The polyallylamine conjugate according to claim 3, wherein the antibody is an anti-IgE antibody.

8. The polyallylamine conjugate according to claim 4, wherein the antibody is an anti-IgE antibody.

9. The polyallylamine conjugate according to claim 5, wherein the antibody is an anti-IgE antibody.

10. The polyallylamine conjugate according to claim 2, wherein the polyallylamine conjugate is in contact with a target molecule.

11. The polyallylamine conjugate according to claim 10, wherein the target molecule is an antigen or on a biochip.

12. The polyallylamine conjugate according to claim 11, wherein the target molecule is an antigen.

13. The polyallylamine conjugate according to claim 12, wherein the antibody is an anti-IgE antibody.

14. The polyallylamine conjugate according to claim 13, wherein the antibody is an anti-IgE antibody.

15. The polyallylamine conjugate according to claim 14, wherein the antibody is an anti-IgE antibody.

* * * * *